US012144774B2

(12) United States Patent
Lee et al.

(10) Patent No.: US 12,144,774 B2
(45) Date of Patent: Nov. 19, 2024

(54) SPASTICITY ASSESSMENT AND REHABILITATION SUPPORT SYSTEM FOR STROKE PATIENTS USING CHARACTERISTIC VECTOR ANALYSIS

(71) Applicant: Seahak Kim, Mukilteo, WA (US)

(72) Inventors: Jongho Lee, Ishikawa (JP); Duk Shin, Shibuya (JP)

(73) Assignee: Seahak Kim, Mukilteo, WA (US)

( * ) Notice: Subject to any disclaimer, the term of this patent is extended or adjusted under 35 U.S.C. 154(b) by 0 days.

(21) Appl. No.: 18/415,941

(22) Filed: Jan. 18, 2024

(65) Prior Publication Data
US 2024/0238145 A1 Jul. 18, 2024

Related U.S. Application Data

(60) Provisional application No. 63/439,791, filed on Jan. 18, 2023.

(51) Int. Cl.
*A61H 1/02* (2006.01)
*A61B 5/00* (2006.01)
(Continued)

(52) U.S. Cl.
CPC .......... *A61H 1/0285* (2013.01); *A61B 5/1107* (2013.01); *A61B 5/1114* (2013.01);
(Continued)

(58) Field of Classification Search
CPC ............ A61H 2230/605; A61H 1/0274; A61H 1/0285; A61H 1/0288; A61H 2201/1635;
(Continued)

(56) References Cited

U.S. PATENT DOCUMENTS

| 2005/0130815 A1* | 6/2005 | Abdoli-Eramaki | A61F 5/026 482/121 |
| 2008/0294074 A1* | 11/2008 | Tong | A63B 21/0058 601/24 |

(Continued)

OTHER PUBLICATIONS

Buchanan et al. "Estimation of Muscle Forces About the Wrist Joint During Isometric Tasks Using an EMG Coefficient Method" 1993 (Year: 1993).*

(Continued)

*Primary Examiner* — Bradley H Philips
*Assistant Examiner* — Savannah L Gabriel
(74) *Attorney, Agent, or Firm* — Alloy Patent Law; Walker Griffin Weitzel

(57) ABSTRACT

The present invention relates to a system for assessing and rehabilitating spasticity in stroke patients, utilizing a novel approach that combines EMG signal analysis with kinematic data of wrist movements. The system comprises a set of electrodes for capturing EMG signals from key wrist muscles, a motion tracking module for monitoring wrist joint movements, and a processing unit for calculating and normalizing wrist joint torque. A distinctive feature is computation of a characteristic vector, indicative of the spasticity state, derived from the moment arms of the involved muscles. The system includes a motorized wrist system, designed to assist wrist movements in a direction countering the spasticity-induced pull, guided by the characteristic vector. This approach allows for personalized rehabilitation, adapting to the patient's specific muscular imbalances. The invention holds promise for enhanced assessment accuracy and tailored therapy in stroke rehabilitation, offering significant benefits for both clinical and home-based rehabilitation settings.

18 Claims, 13 Drawing Sheets

(51) Int. Cl.
*A61B 5/11* (2006.01)
*A61B 5/389* (2021.01)

(52) U.S. Cl.
CPC ............ *A61B 5/389* (2021.01); *A61B 5/4842* (2013.01); *A61B 5/7225* (2013.01); *A61H 2201/1207* (2013.01); *A61H 2201/1635* (2013.01); *A61H 2201/501* (2013.01); *A61H 2201/5043* (2013.01); *A61H 2201/5079* (2013.01); *A61H 2201/5084* (2013.01); *A61H 2230/605* (2013.01)

(58) Field of Classification Search
CPC .......... A61H 2205/06; A61H 2205/062; A61H 2205/065; A61H 2205/067; A61F 5/013; A61F 5/0118; A61F 5/0102
See application file for complete search history.

(56) References Cited

U.S. PATENT DOCUMENTS

| | | | |
|---|---|---|---|
| 2009/0227925 A1* | 9/2009 | McBean | A61H 1/008 602/16 |
| 2012/0029399 A1* | 2/2012 | Sankai | A61H 1/0288 601/40 |
| 2018/0177666 A1* | 6/2018 | Tsui | A61H 1/0288 |

OTHER PUBLICATIONS

Heung et al. "Soft Rehabilitation Actuator With Integrated Post-stroke Finger Spasticity Evaluation" Feb. 28, 2020 (Year: 2020).*
Ziai et al. "Comparison of regression models for estimation of isometric wrist joint torques using surface electromyography" 2011 (Year: 2011).*
Cha et al. "Quantitative Modeling of Spasticity for Clinical Assessment, Treatment and Rehabilitation" Sep. 5, 2020 (Year: 2020).*

* cited by examiner (A) Changes in the wrist movements during recovery with rehabilitation (B) Changes in the characteristic vector $\vec{P}$ during recovery with rehabilitation

SPASTICITY ASSESSMENT AND REHABILITATION SUPPORT SYSTEM FOR STROKE PATIENTS USING CHARACTERISTIC VECTOR ANALYSIS

The present application hereby claims priority to and incorporates by reference the entirety of the disclosures of the provisional application No. 63/439,791 entitled "Spasticity Force Assist and Characteristic Vector Calculation Method" filed on 18 Jan. 2023.

FIELD OF THE INVENTION

The present invention relates generally to medical diagnostic systems. More specifically, it pertains to systems designed to assess and support rehabilitation in stroke patients. It focuses on the use of characteristic vector analysis for evaluating spasticity, a common symptom in stroke survivors.

BACKGROUND

Stroke, a leading cause of disability worldwide, often results in spasticity, a motor disorder characterized by a velocity-dependent increase in tonic stretch reflexes. Spasticity can significantly impair a patient's functional recovery and quality of life. Traditional methods of assessing spasticity, such as the Modified Ashworth Scale and Tardieu Scale, rely on subjective evaluations by clinicians, leading to potential variability and inconsistency in assessments. Recent advances in medical technology have enabled more precise and objective evaluations of muscle tone and reflexes. One such advancement is the use of characteristic vector analysis. This method involves collecting and analyzing data from various sensors and input devices to create a multidimensional vector that represents the patient's specific spasticity profile. This profile not only offers a more detailed and objective assessment of the patient's condition but also allows for tailored rehabilitation strategies.

The proposed system integrates sensor technology, data analysis, and rehabilitation protocols into a comprehensive solution for stroke patients. It utilizes sensors to measure muscle tone, reflexes, and other relevant parameters, which are then processed to generate a characteristic vector representing the patient's spasticity status. This vector can be monitored over time to track progress and adjust rehabilitation strategies accordingly. In the broader context, this invention addresses the need for more accurate and personalized approaches to managing spasticity in stroke patients. It aligns with current trends in healthcare towards precision medicine and data-driven treatment plans. By providing a tool that can objectively assess and monitor spasticity, this system has the potential to improve rehabilitation outcomes and enhance the quality of life for stroke survivors.

SUMMARY

The present invention pertains to innovative solutions and embodiments devised to rectify prevalent shortcomings.

The invention in discussion presents an advanced system designed for the assessment and rehabilitation of spasticity in stroke patients. This system innovatively combines electromyography (EMG) signal analysis with detailed kinematic data of wrist movements, offering a comprehensive approach to understand and address the challenges of post-stroke spasticity. At the core of the system is a set of electrodes, specifically designed to record EMG signals from at least eight key muscles involved in wrist movements. This setup ensures a thorough capture of muscular activities, crucial for analyzing muscle function and coordination. Alongside EMG signal recording, the system includes a sophisticated motion tracking module. This module is responsible for tracking the kinematics of the wrist joint, including parameters such as wrist angle, angular velocity, and angular acceleration. By monitoring this kinematics in real-time, the system gains a detailed understanding of the physical movements of the wrist, essential for correlating with EMG data. The processing unit of the system stands out for its capability to calculate wrist joint torque from the kinematic data using a precise equation of motion, using a bandwidth pass filter with a 0.01~2.5 Hz. This calculation is pivotal in understanding the mechanical forces at play during wrist movements. Furthermore, the processing unit normalizes the recorded EMG signals. This normalization, based on a constant joint torque established through an isometric contraction task, accounts for variabilities such as skin resistance and electrode placement, ensuring the accuracy of muscle activity readings. One of the most innovative aspects of this invention is the computational module designed to determine the moment arms for each muscle. Utilizing a least squares optimization method, the module analyzes the normalized EMG signals in conjunction with the calculated wrist joint torque. This analysis is crucial for developing the characteristic vector, a unique element of the invention. The characteristic vector is a quantifiable representation of the state of spasticity in the patient, derived from the moment arms of the muscles involved in wrist movements. The characteristic vector informs the rehabilitation process by indicating the severity and direction of spasticity. This information is used to tailor wrist movement assistance provided by the motorized wrist system, which forms an integral part of the invention. The motorized system assists the wrist movements in a direction opposite to that indicated by the characteristic vector, effectively counteracting the spasticity. This targeted approach ensures that the rehabilitation exercises are highly personalized and directly address the specific challenges faced by each stroke patient. In summary, this invention provides a holistic and data-driven solution for assessing and rehabilitating spasticity in stroke patients. Its integration of EMG signal analysis, kinematic data tracking, and personalized motor-assisted rehabilitation offers a novel and effective approach to stroke care. The system not only enhances the accuracy of spasticity assessment but also ensures that rehabilitation exercises are optimally tailored to individual patient needs. By bridging the gap between muscular activity and physical movement, the invention holds significant potential for improving the quality of life for stroke survivors, offering a path to more effective recovery and greater independence.

BRIEF DESCRIPTION OF THE ACCOMPANYING DRAWINGS

The novel features which are believed to be characteristic of the present invention, as to its structure, organization, use, and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

Figure 1:
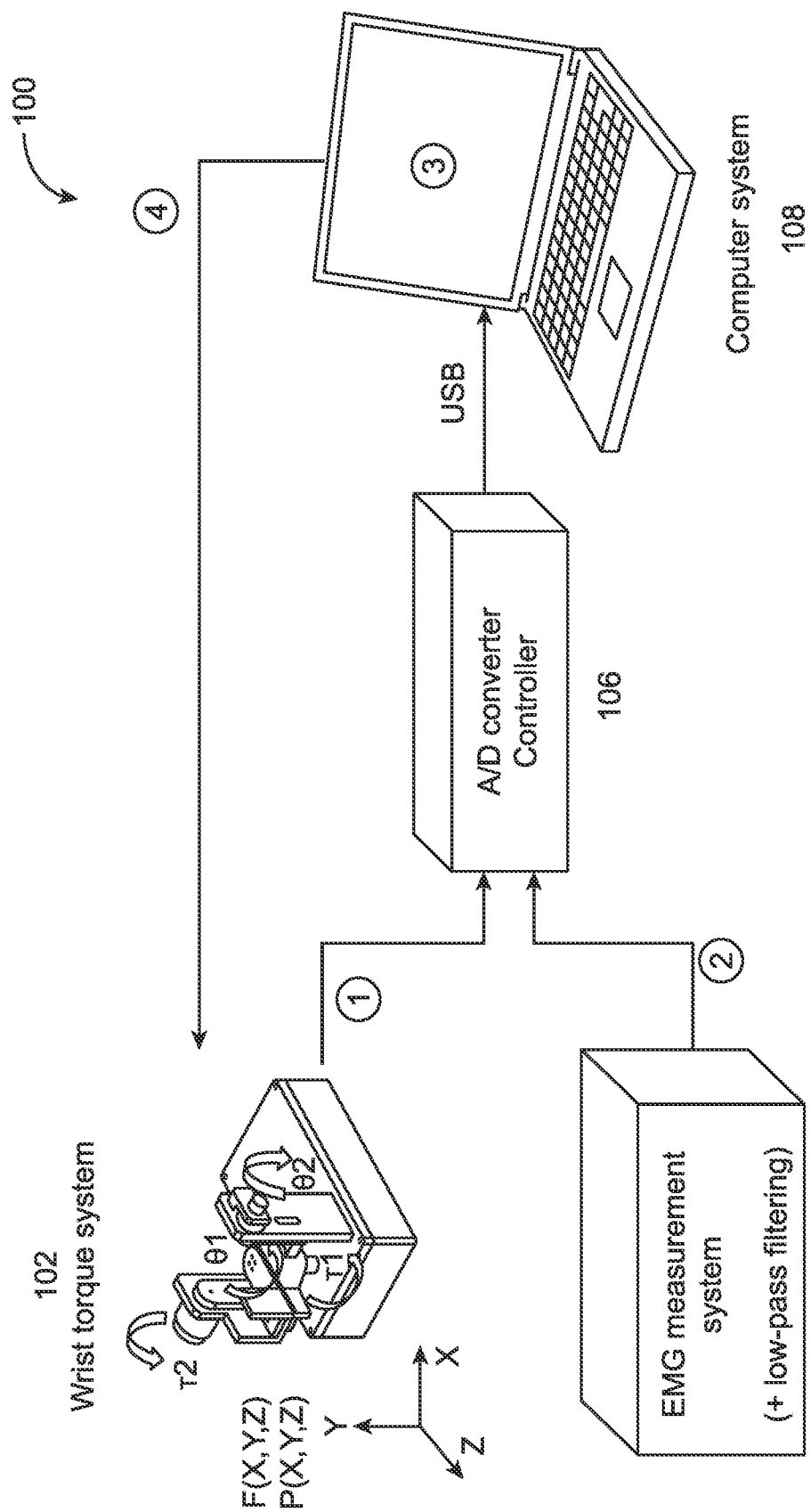
FIG. 1 is a diagram that illustrates rehabilitation support and training using characteristic vectors, in accordance with an embodiment of the present invention.

Further areas of applicability of the present invention will become apparent from the detailed description provided hereinafter. It should be understood that the detailed description of exemplary embodiments is intended for illustration purposes only and is, therefore, not intended to necessarily limit the scope of the invention.

DETAILED DESCRIPTION

As used in the specification and claims, the singular forms "a", "an" and "the" may also include plural references. For example, the term "an article" may include a plurality of articles. Those with ordinary skill in the art will appreciate that the elements in the Figures are illustrated for simplicity and clarity and are not necessarily drawn to scale. For example, the dimensions of some of the elements in the Figures may be exaggerated, relative to other elements, to improve the understanding of the present invention. There may be additional components described in the foregoing application that are not depicted on one of the described drawings. In the event such a component is described, but not depicted in a drawing, the absence of such a drawing should not be considered as an omission of such design from the specification.

It should be observed that the present invention utilizes a combination of components or set-ups, which constitutes systems designed to assess and support rehabilitation in stroke patients. It focuses on the use of characteristic vector analysis for evaluating spasticity, a common symptom in stroke survivors. Accordingly, the components have been represented, showing only specific details that are pertinent for an understanding of the present invention so as not to obscure the disclosure with details that will be readily apparent to those with ordinary skill in the art having the benefit of the description herein. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

References to "one embodiment", "an embodiment", "another embodiment", "yet another embodiment", "one example", "an example", "another example", "yet another example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

The words "comprising," "having," "containing," and "including," and other forms thereof, are intended to be equivalent in meaning and be open ended in that an item or items following any one of these words is not meant to be an exhaustive listing of such item or items or meant to be limited to only the listed item or items. Unless stated otherwise, terms such as "first" and "second" are used to arbitrarily distinguish between the elements. Thus, these terms are not necessarily intended to indicate temporal or other prioritization of such elements. While various exemplary embodiments of the disclosed invention have been described below it should be understood that they have been presented for purposes of example only, not limitations. It is not exhaustive and does not limit the invention to the precise form disclosed. Modifications and variations are possible considering the above teachings or may be acquired from practicing of the invention, without departing from the breadth or scope.

The invention will now be described with reference to the accompanying drawings which should be regarded as merely illustrative without restricting the scope of the present invention.

FIG. 1 is a diagram 100 that illustrates rehabilitation support and training using characteristic vectors, in accordance with an embodiment of the present invention. This is an illustration of a system providing rehabilitation support and training to stroke patients, utilizing characteristic vectors for personalized therapy. The diagram 100 includes a wrist torque system 102, an EMG measurement system 104, an Analog-to-Digital (A/D) converter controller 106, and a computer system 108.

In an embodiment, the wrist torque system 102 is a specialized device designed to measure and apply torque to the wrist joint. In the context of stroke rehabilitation, it may be used to assess the strength and flexibility of the wrist, as well as to provide resistance training. The system might include mechanisms for precisely controlling and measuring the force applied to the wrist, allowing for detailed analysis and tailored rehabilitation exercises. The wrist torque system 102 may include a processing unit configured to calculate wrist joint torque based on the kinematics using an equation of motion and to normalize the recorded EMG signals based on a constant joint torque using an isometric contraction task. The isometric contraction task for normalization is based on a constant joint torque, the around maximum exertable torque by a patient.

In an embodiment, EMG, or Electromyography, is a technique for recording the electrical activity produced by skeletal muscles. The EMG measurement system 104 may be used to monitor the muscle activity in the forearm and wrist areas. This data is crucial for understanding muscle function and coordination, particularly in patients recovering from a stroke. The system includes electrodes that are attached to the skin and an amplifier to boost the signal for analysis.

In an embodiment, the Analog-to-Digital (A/D) converter controller 106 is a device that converts analog signals (like those from the EMG system) into digital data that a computer (such as the computer system 108) can process. The USB interface suggests that it is designed for easy connectivity with standard computer systems. This component is essential for digitizing the analog signals from the EMG system 104 and the wrist torque system 102, allowing for detailed data analysis and storage.

In an embodiment, the computer system 108 is the central unit that controls the entire setup and processes the data collected from the other systems. The computer system 108 may be equipped with specialized software for analyzing the torque and EMG data, monitoring patient progress, and possibly even controlling the wrist torque system for various exercises. It may also include visualization tools to display the data in an interpretable manner for clinicians and patients, and databases for storing patient information and progress over time.

Figure 2:
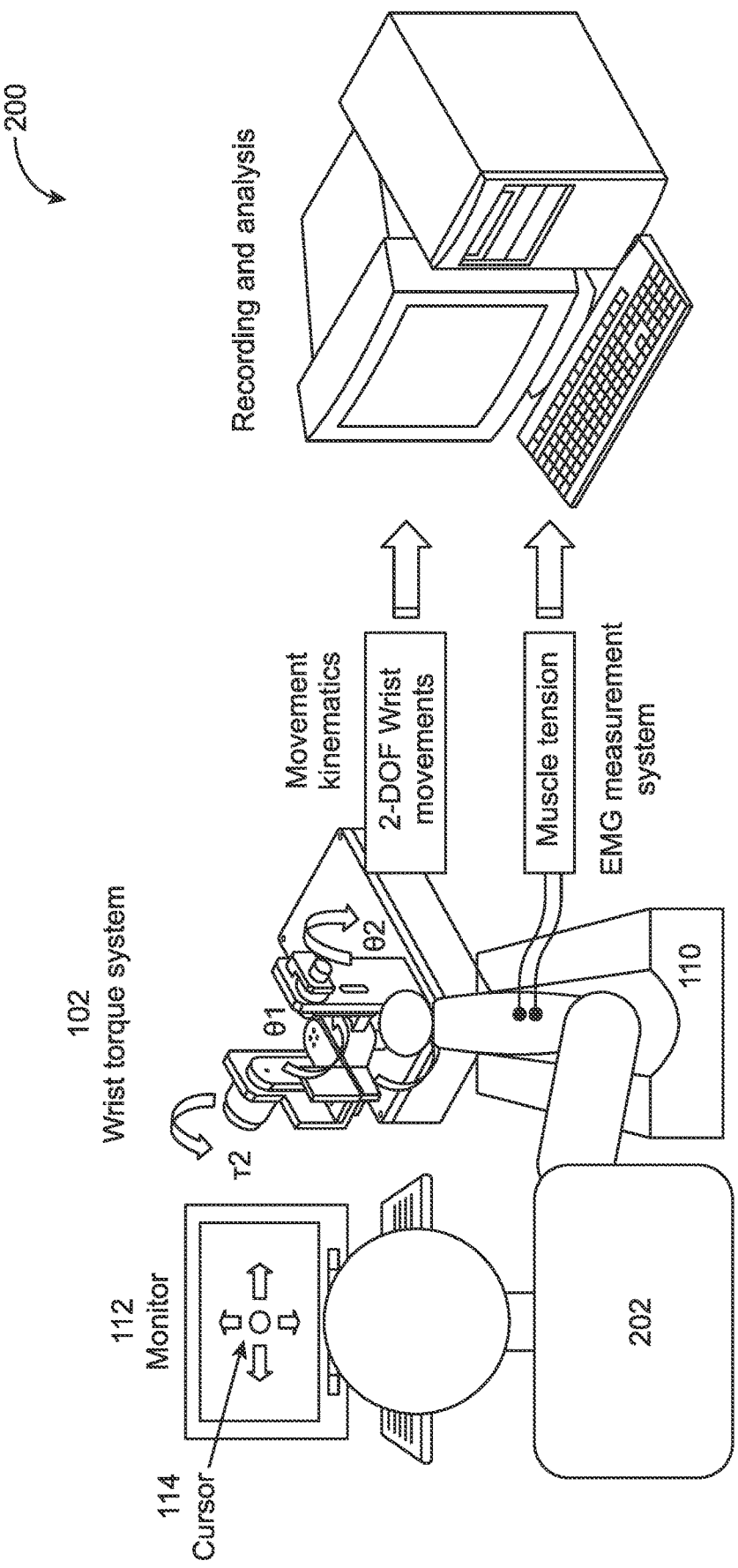
FIG. 2 is a diagram that illustrates an overview of the experiment using the wrist torque system, in accordance with an embodiment of the present invention.

FIG. 2 is a diagram 200 that illustrates an overview of the experiment using the wrist torque system, in accordance with an embodiment of the present invention. This is a schematic representation of the experimental setup, showing the wrist torque system used to assess and analyze wrist movements in patients.

The present invention discloses a method for assessing the spasticity status of stroke patients and providing rehabilitation support using a sophisticated analysis of the causal relationship between motor commands and physical movements. The focus is on the interaction between electromyography (EMG) signals, which represent the motor commands from the brain (the cause), and the resulting movements of the wrist joint (the effect). This relationship is represented in FIG. 1 of the present invention, where the wrist movements (1) and EMG signals (2) play a central role.

The disclosed system includes two key components: the wrist torque system 102 and the EMG signal measurement system 104, as shown in FIG. 1. The wrist torque system 102, as shown in FIG. 2, has been designed to measure and control the movements of the wrist with high precision. In a typical setup, a subject user 202 may sit and rest their forearm on an armrest 110, grasping the manipulandum of the wrist torque system 102. This setup may allow for the measurement of wrist movements in two degrees of freedom: extension-flexion and radial-ulnar flexion. The movements may be captured by two position sensors on the manipulandum, translating physical movements into digital data. These wrist movements are then visually represented on a computer screen 112, typically as a small cursor 114 such as black dot 2 mm in diameter. This cursor movement may be directly linked to the subject's wrist actions. For example, if the subject user 202 moves their wrist in flexion, the cursor moves left; if they extend the wrist, the cursor moves right. Similarly, the radial and ulnar deviations result in the cursor moving up or down, respectively. This visual representation allows for precise monitoring and feedback on the wrist's movements. The target was displayed as a circle, and the diameter of the target (1 cm) corresponded to a wrist movement of 4.5°. Concurrently, the EMG signal measurement system 104 may record the electrical activity of the muscles involved in these wrist movements. These signals are the physical manifestation of motor commands issued by the brain. By analyzing these EMG signals, the system can deduce the nature of the neural commands being sent to the muscles.

The core innovation of the present invention lies in how it uses these two streams of data i.e., the physical movements of the wrist and the EMG signals, to assess spasticity in stroke patients. It does so by identifying characteristic vectors that emerge from the causal relationship between the motor commands (EMG signals) and the resultant wrist movements. These vectors are a mathematical representation that captures the essence of this cause-and-effect relationship. A characteristic vector calculator may be employed for determining a vector indicating the state of spasticity based on the moment arms. In a rehabilitation context, understanding this relationship is crucial. Spasticity, a common condition in stroke survivors, may be characterized by increased muscle tone and overactive reflexes. By analyzing how motor commands translate into physical movements, the system can pinpoint abnormalities or changes in muscle behavior. This insight is invaluable in both diagnosing the severity of spasticity and in tailoring rehabilitation exercises to the patient's specific needs.

The use of a visual cursor 114 on the computer screen 112 linked to the patient's wrist movements serves multiple purposes. It provides immediate feedback to the patient, allowing them to understand and adapt their movements in real-time. It also enables clinicians to observe and record these movements in a quantifiable manner, making it easier to track progress over time.

Figure 3:
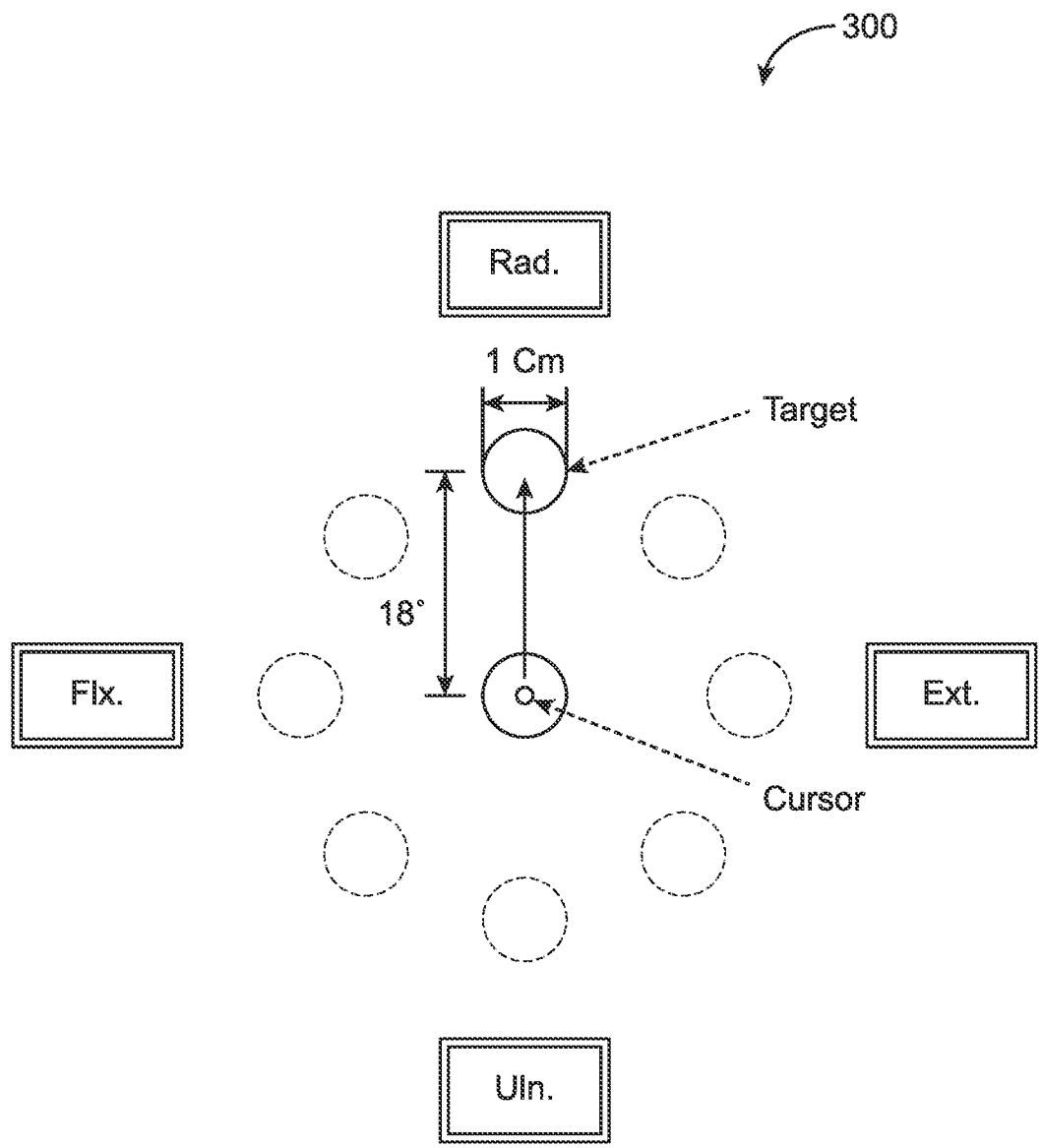
FIG. 3 is a diagram that illustrates step-tracking task performed, in accordance with an embodiment of the present invention.

FIG. 3 is a diagram 300 that illustrates step-tracking task performed, in accordance with an embodiment of the present invention. This is a schematic depicting the step-tracking task process, an integral part of the rehabilitation program, illustrating how patients interact with the system. The movement task, (1) of FIG. 1, is a critical component of the present invention. It involves a step-tracking movement task (as shown in FIG. 3) that is designed to assess the motor function and control in stroke patients, specifically focusing on the wrist's movements. This task examines the wrist's two degrees of freedom and consists of movements in eight distinct directions, providing a comprehensive assessment of the wrist's functional capabilities.

Description of the Task:
  Task Setup: The task may be performed using a computer interface where a cursor represents the wrist's position. The initial position of the cursor is at the center of the screen (X=0°, Y=0°), corresponding to the neutral position of the wrist.
  Execution of Movements: Upon starting a trial, the subject user 202 (FIG. 2) may be required to keep the cursor inside a central target for a brief hold period (1-2 seconds). After this period, the target moves to one of the eight designated locations around the center, each corresponding to an 18° movement of the wrist joint from the central position. These eight targets represent the full range of wrist movements in the two degrees of freedom (extension-flexion and radial-ulnar flexion).

Subject's Task: The subject user may move the cursor to the new target location as quickly and accurately as possible. After reaching the target and another variable hold period, the target returns to the central position, signaling the end of the trial and the commencement of the next.

In an embodiment, this movement task may be designed to simulate real-world wrist movements and to challenge the subject's motor control abilities. By requiring rapid and accurate movements in various directions, the task effectively assesses the subject's ability to send appropriate motor commands to the wrist muscles. This is particularly relevant for stroke patients, where motor command efficiency can be impaired.

Data Recording and Data Analysis ((2) and (3) in FIG. 1)

Data Recording:

Setup: The setup may involve recording two types of data: the position of the wrist (X, Y coordinates) and EMG signals.

Wrist Position: The position of the wrist may be tracked through the cursor's movements on the computer screen, corresponding to the actual wrist movements in real-time.

EMG Signals: EMG signals may be recorded from eight electrodes placed on the subject's forearm. These electrodes are specifically positioned over the four prime movers of the wrist: extensor carpi radialis (ECR), extensor carpi ulnaris (ECU), flexor carpi ulnaris (FCU), and flexor carpi radialis (FCR).

Sampling Rate: Both the wrist position data and EMG signals may be recorded at a high sampling rate of 2 kHz, ensuring detailed and accurate data capture.

Data Analysis:

Objective: The primary goal of data analysis in this context is to understand the causal relationship between the motor commands (as evidenced by EMG signals) and the resulting wrist movements.

Process: Analysis may involve examining how the motor commands from the brain translate into physical movements of the wrist. This requires sophisticated algorithms that can interpret the high-frequency data, identifying patterns and correlations between the EMG signals and the wrist's movements.

By analyzing this data, researchers can gain insights into the efficiency and effectiveness of the motor commands post-stroke. This is crucial in understanding the level of spasticity and motor control impairment in stroke patients. It also helps in tailoring rehabilitation exercises to the patient's specific needs, enhancing the recovery process. In summary, the movement task ((1) in FIG. 1) is designed to simulate realistic wrist movements and challenge the motor control of stroke patients. The data recording process ((2) in FIG. 1) captures detailed information about wrist positions and muscle activity through EMG signals. The data analysis part ((3) in FIG. 1) then delves into this data to unravel the complex relationship between brain commands and physical movements. This comprehensive approach provides a deeper understanding of motor function impairments in stroke survivors and aids in developing more effective rehabilitation strategies.

Figure 4:
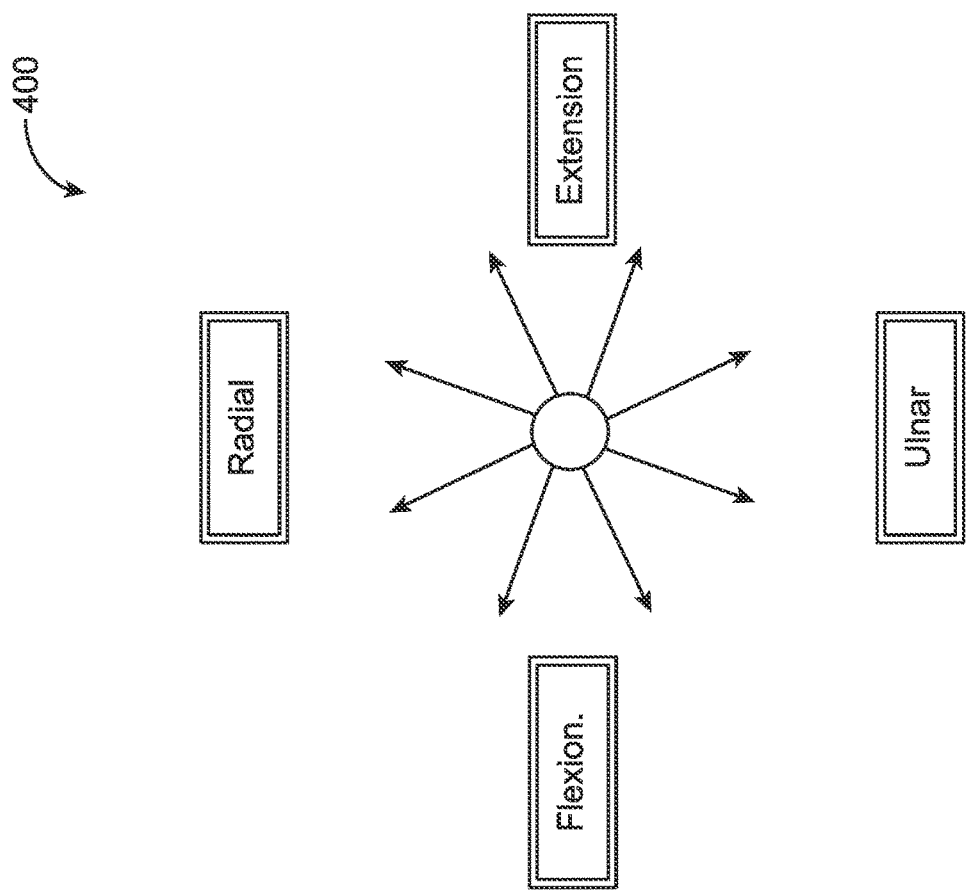
FIG. 4 is a diagram that illustrates electrode locations and muscle action directions for wrist movements, in accordance with an embodiment of the present invention.
Figure 4:
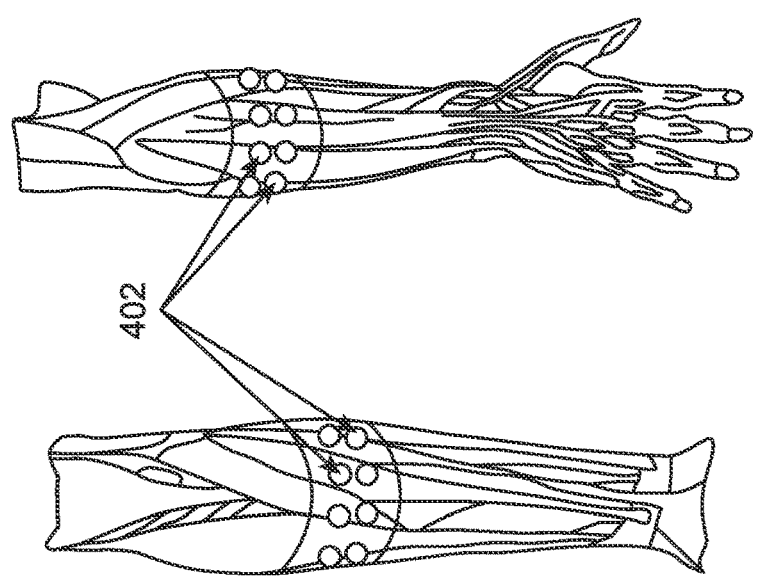

FIG. 4 is a diagram 400 that illustrates electrode locations and muscle action directions for wrist movements, in accordance with an embodiment of the present invention. Two-part figure; the left shows the placement of eight electrodes on a patient's wrist, and the right details the directional mechanical action of muscles recorded by each electrode.

In an embodiment, the eight electrodes 402 are strategically placed on the forearm to capture EMG signals from specific muscles involved in wrist movements. These placements may be designed to comprehensively cover the muscles responsible for the two degrees of freedom (DOF) movements of the wrist joint, including extension-flexion and radial-ulnar flexion. The electrodes are Ag—AgCl (silver-silver chloride) electrodes pairs, known for their effectiveness in capturing bioelectrical signals like EMG. They may be spaced 10 mm apart to ensure accurate signal detection.

In an embodiment, the right figure in FIG. 4 indicates the direction of the mechanical action of each muscle recorded by the electrodes 402. This information is vital because it helps in understanding how each muscle contributes to the various movements of the wrist. By knowing the direction of muscle action, researchers may correlate specific muscle activations with particular wrist movements, aiding in the analysis of the causal relationship between muscle activity and wrist motion.

In an embodiment, the EMG signals captured by the electrodes 402 are first digitally rectified. Rectification is a process of converting all negative values of the EMG signal to positive, making the data easier to analyze. After rectification, the signals are filtered using a second-order low-pass filter with a cut-off frequency of 5.0 Hz. This filtering is crucial for removing high-frequency noise from the EMG signals, ensuring that only relevant muscle activity data is retained. The choice of a second-order low-pass filter and a 5 Hz cutoff frequency may be based on standard practices in neurophysiological studies. This setup, particularly a second-order Butterworth filter, is known to be effective for EMG signal analysis.

In an embodiment, the magnitude of the low-pass filtered EMG signal ($\overline{EMG}_i$, i=1, . . . , 8) may be proportional to the muscle tension. This proportionality allows for the estimation of muscle tensions from surface EMG signals. The filtered EMG signals are thus referred to as 'muscle tension.' By analyzing these tensions, researchers can estimate the torque at the wrist joint. This estimation is fundamental to understanding how muscle activities translate into wrist movements.

Figure 5:
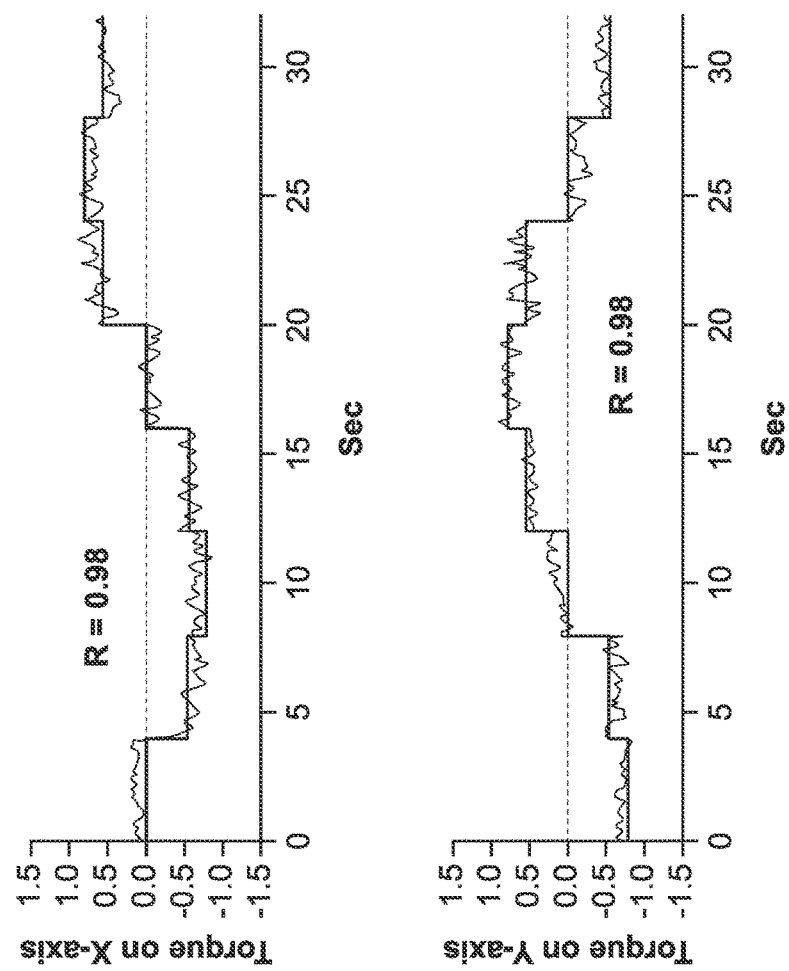
FIG. 5 is a diagram that illustrates normalization of muscle tension using the isometric contraction task, in accordance with an embodiment of the present invention.
Figure 5:
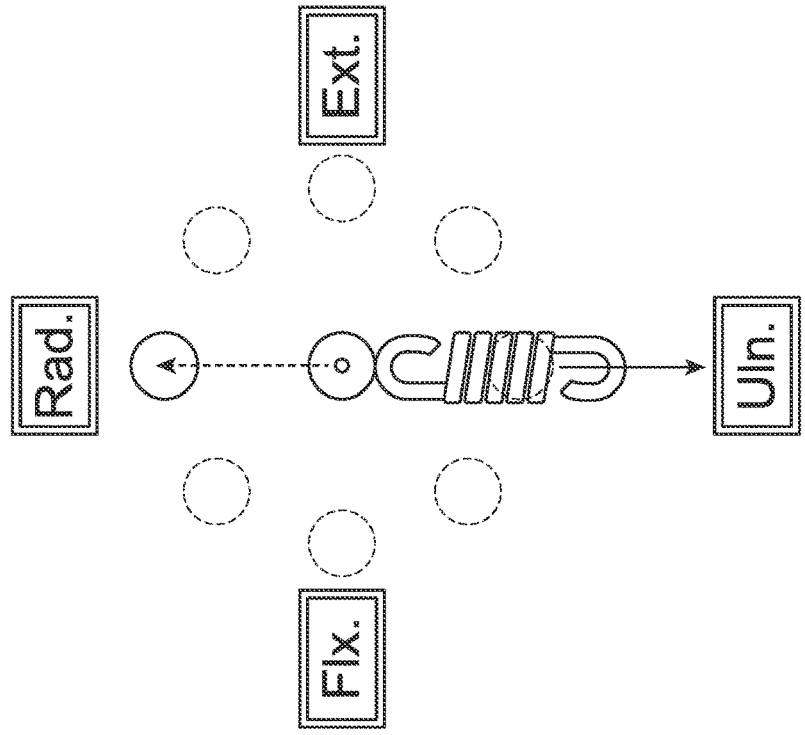
Figure 5:
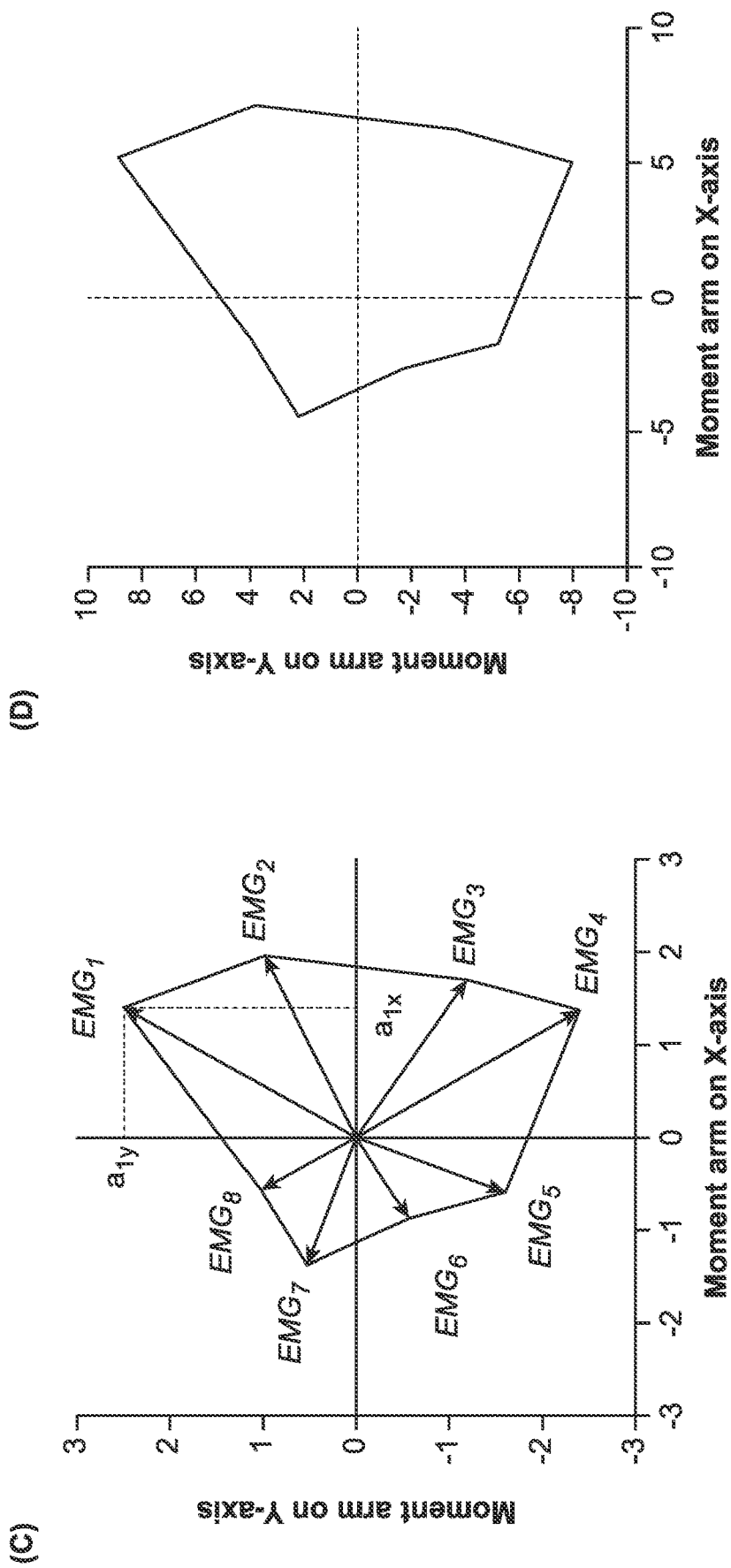

FIG. 5 is a diagram 500 that illustrates normalization of muscle tension using the isometric contraction task, in accordance with an embodiment of the present invention. A multi-part figure demonstrating the process of normalizing muscle tension; includes (A) the isometric contraction task at the wrist joint, (B) the least-squares optimization method, (C) identification of muscle moment arms, and (D) an example of moment arms data from a subject.

In an embodiment, the magnitude of muscle tension represented by EMG signals ($\overline{EMG}_i$, i=1, . . . , 8) may not be consistent across different conditions due to factors like skin resistance and electrode placement. To ensure accuracy, it is necessary to normalize these EMG signals to account for these variabilities. In an embodiment, an isometric contraction task, depicted in FIG. 5A, may be used for normalization. Here, EMG signals are recorded while the subject maintains a constant joint torque (e.g., 0.784 Nm). This setting provides a controlled environment to accurately measure muscle tensions. The aim is to establish a standard or baseline level of muscle tension against which all subsequent measurements can be compared.

Moment arms ($\vec{a}_{ix}$ and $\vec{a}_{iy}$, i=1, . . . , 8) are determined for each muscle, for example, by using a computational module based on the normalized EMG signals and the calculated wrist joint torque using a least squares optimization method. The processing unit is configured to calculate wrist joint torque using a bandwidth-pass filter with a 0.01~2.5 Hz. These are the lever arms through which the muscle force acts on the wrist joint. The moment arms are calculated by matching the linear sum of the eight muscle tensions with the wrist joint torque ($\vec{\tau}_x$ and $\vec{\tau}_y$) during isometric contraction. The equations used are as follows:

$$\vec{\tau}_x = \sum_{i=1}^{8} \overline{EMG_i} \cdot \vec{a}_{ix} \qquad (1\text{-}1)$$

$$\vec{\tau}_y = \sum_{i=1}^{8} \overline{EMG_i} \cdot \vec{a}_{ix} \qquad (1\text{-}2)$$

The least-squares method, an optimization technique, may be applied to these equations to find the best-fit values for the moment arms. This method minimizes the total squared difference between the observed muscle tensions and the predicted values based on the moment arms.

FIG. 5B shows an example of these optimization results. It represents how well the calculated moment arms align with the actual muscle tensions recorded during the isometric task. FIG. 5C depicts the moment arms for each muscle, indicated by arrows. These visual representations help in understanding the direction and magnitude of the forces exerted by each muscle on the wrist joint. FIG. 5D further illustrates how these moment arms are interconnected and how they function collectively in a specific subject.

Once the moment arms are determined, they are used to normalize the EMG signals during wrist movements. This means the moment arms obtained from the optimization process are multiplied by the EMG signals (muscle tension) of each muscle. This normalization process adjusts the raw EMG signals to account for individual differences in muscle leverage and electrode placement, leading to more accurate assessments of muscle activity. The normalized EMG signals are then interpreted as indicators of muscle activity ($nEMG_i$, i=1, . . . , 8) representing motor commands from the brain. This interpretation is crucial for understanding how the brain's neural signals translate into physical movements, especially in assessing the motor function of stroke patients. The process of normalizing muscle tension using EMG signals and the subsequent determination of moment arms are fundamental to accurately evaluating the muscle activities and wrist joint torque. This method allows for a more precise understanding of the causal relationship between brain commands (as reflected in muscle activities) and the resultant wrist movements. It provides valuable insights into the motor control capabilities of stroke patients, essential for designing effective rehabilitation strategies tailored to their specific needs. By normalizing and analyzing these signals, the invention achieves a higher level of accuracy in assessing and addressing motor function impairments in stroke survivors.

Figure 6:
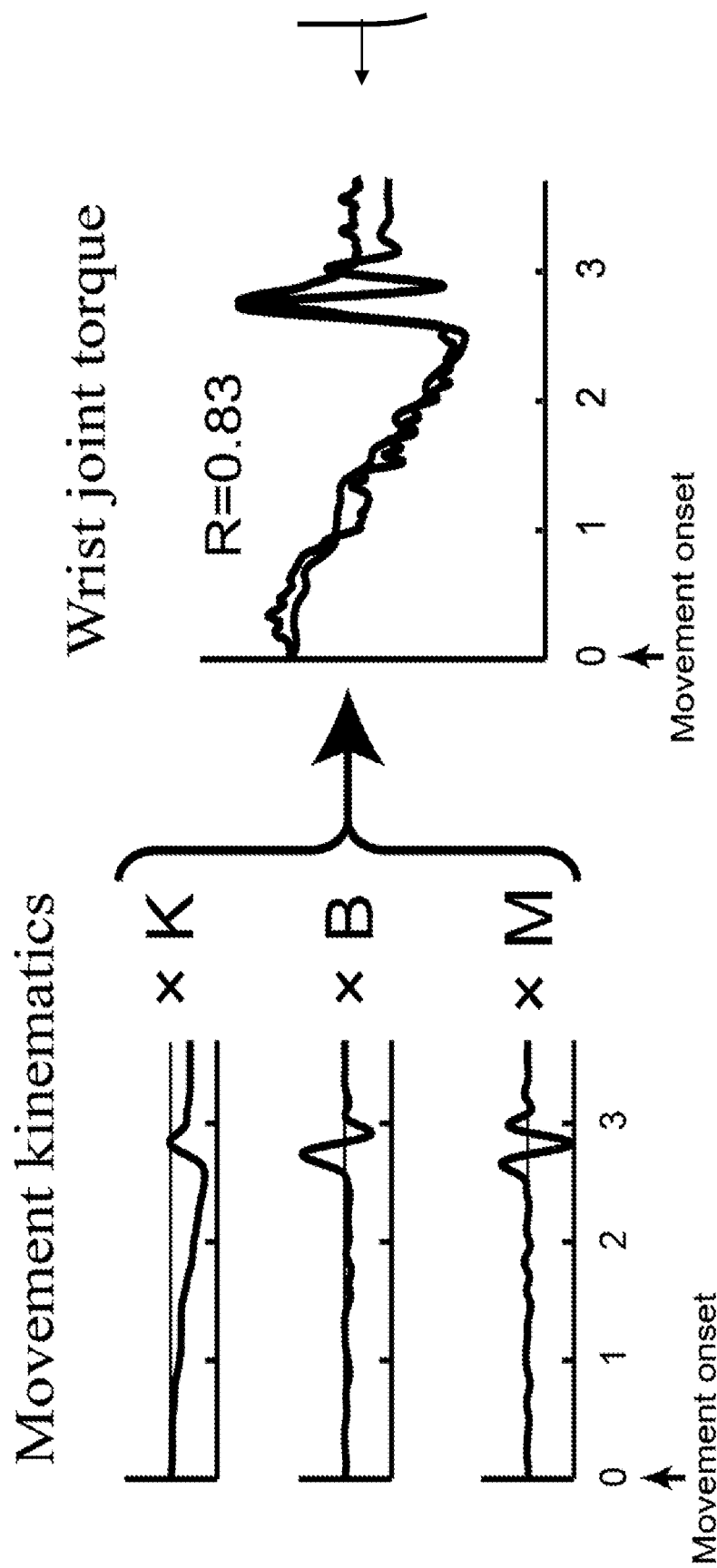
FIG. 6 is a diagram that illustrates identifying causal relationship between EMG signals and wrist movement kinematics, in accordance with an embodiment of the present invention.
Figure 6:
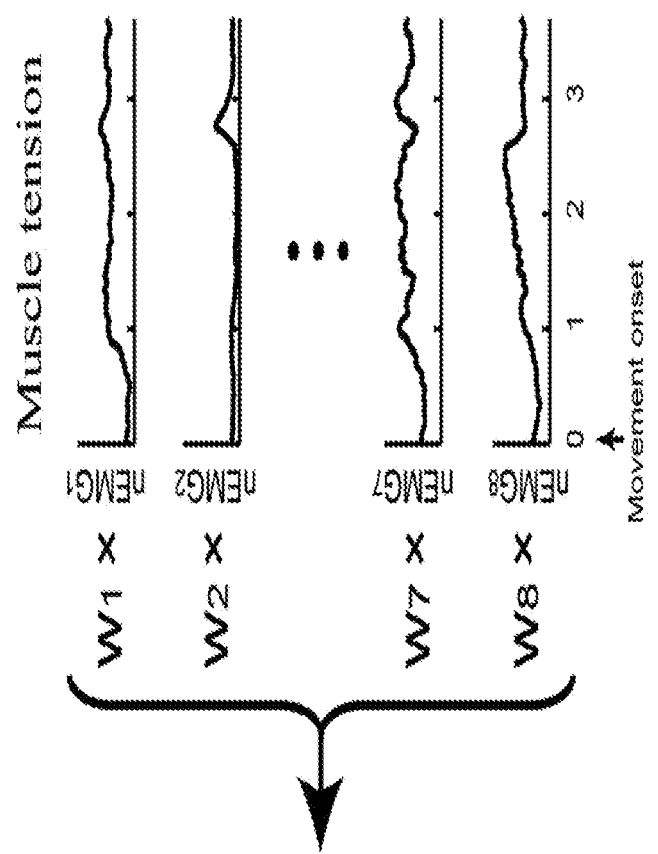

FIG. 6 is a diagram 600 that illustrates identifying causal relationship between EMG signals and wrist movement kinematics, in accordance with an embodiment of the present invention. A graphical representation showing the correlation between EMG (electromyography) signals (causal) and the resultant kinematics of wrist movements at the wrist joint torque level. In FIG. 6, the invention outlines a method to identify the causal relationship between muscle activity from motor commands and the resulting movement kinematics at the wrist joint torque level. This process involves two main steps: calculating the wrist joint torque from the kinematics of wrist joint motion including wrist angle, angular velocity, and/or angular acceleration (for example, by using a motion tracking module) and determining transformation factors for each muscle to match this torque with the muscle activities.

We first calculated the wrist joint torque from the kinematics of wrist joint motion using the equation of motion in equation (2), as shown in left figure in FIG. 6.

$$\vec{\tau}_{kin} = M\ddot{\theta} + B\dot{\theta} + K\theta \qquad (2)$$

Here, $\vec{\tau}_{kin}$ is the wrist joint torque obtained from the kinematics of wrist joint motion (blue in the middle figure of FIG. 6), and $\theta$, $\dot{\theta}$, $\ddot{\theta}$ are the wrist angle, angular velocity, and angular acceleration. M is the moment of inertia, which is obtained by assuming the hand to be a rigid body. B and K are the viscosity and elasticity coefficients, and B=0.03 Nms/rad and K=0.2 Nm/rad based on the values reported from previous research.

We then determined transformation factors of each muscle, $w_{1x\sim 8x}$ and $w_{1y\sim 8y}$ so that the linear sum of the eight muscle activities ($nEMG_i$, i=1, . . . , 8) matches the wrist joint torque using the least square optimization method based on equation (3).

$$\vec{\tau}_{EMG} = \sum_{i=1}^{8} W_i \cdot nEMG_i \qquad (3)$$

The viscosity coefficient is set to B Nms/rad and the elasticity coefficient is set to K Nm/rad as shown in FIG. 6. The K and B are match up factors between equations (2) and (3). The process essentially correlates the mechanical aspects of wrist motion (torque, angle, velocity, acceleration) with the physiological aspects (muscle activity). This correlation is crucial in understanding the causal relationship between motor commands and resultant wrist movements, especially in the context of stroke rehabilitation.

Figure 7:
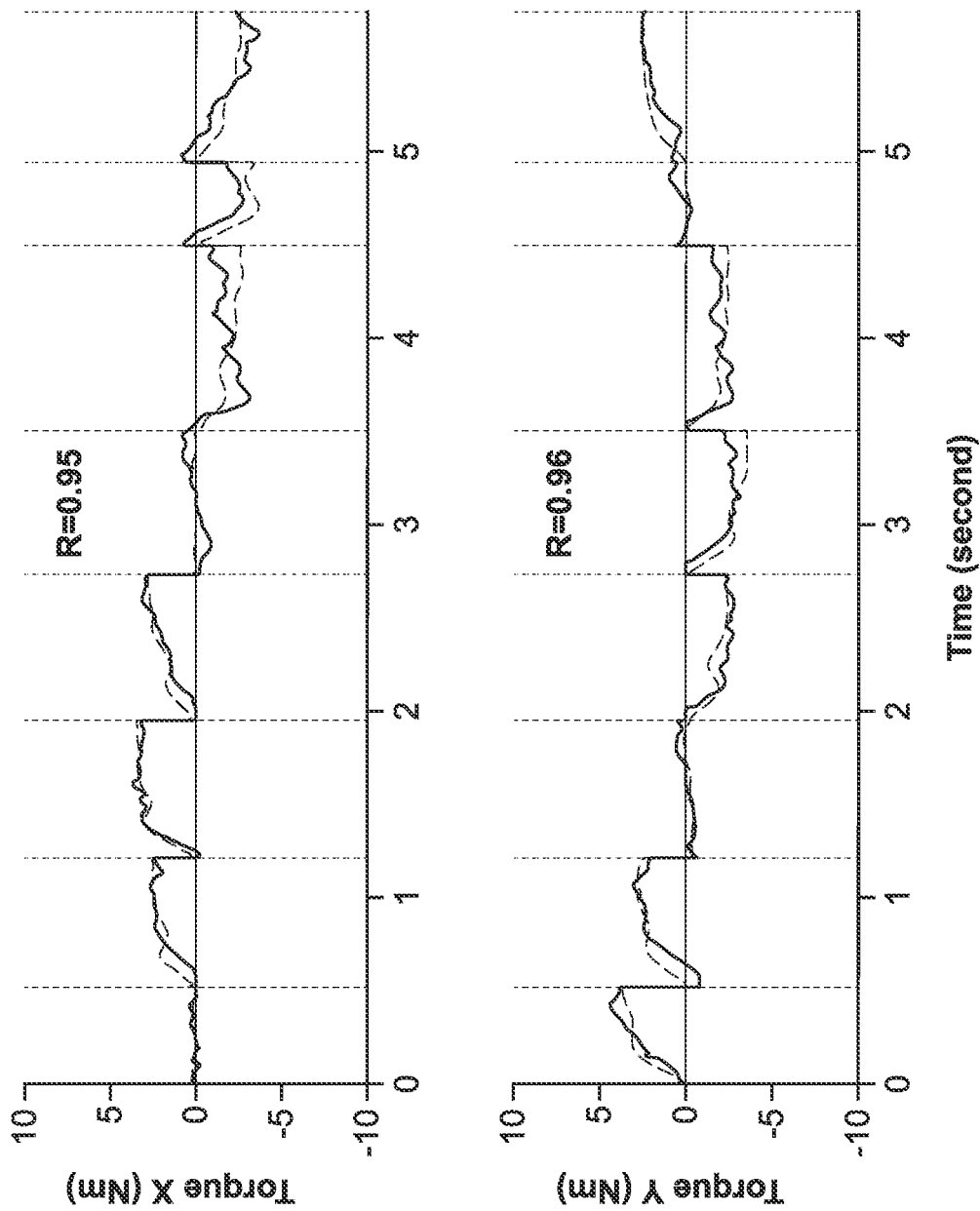
FIG. 7 is a diagram that illustrates results of identifying causal relationship in step-tracking task, in accordance with an embodiment of the present invention.

FIG. 7 is a diagram 700 that illustrates results of identifying causal relationship in step-tracking task, in accordance with an embodiment of the present invention. Results displayed from the analysis of the causal relationship between EMG signals and wrist movements in an eight-direction step-tracking task. FIG. 7 shows that the kinematic torque ($\vec{\tau}_{kin}$) calculated from the wrist joint motion data and the muscle torque ($\vec{\tau}_{EMG}$) calculated from the EMG signals are identical in the X-axis (upper figure) and Y-axis (bottom figure) of the 8 directional step-tracking movements. The blue lines in FIG. 7 are the kinematic torque ($\vec{\tau}_{kin}$), and the red lines in FIG. 7 are the muscle torque ($\vec{\tau}_{EMG}$). As shown in FIG. 7, we confirmed that there is a very high correlation (correlation coefficients R=0.95 and 0.96) between the two-wrist joint torques. This result means that the causal relationship between the casual EMG signals and the resultant wrist movements is identical using the eight muscle activities ($nEMG_i$, i=1, . . . , 8: right figure in FIG. 6).

In essence, FIG. 7 reinforces the validity of the approach used in the invention to establish a clear and quantifiable link between muscle activities and wrist joint movements. The high correlation between kinematic torque and muscle torque underscores the precision of the methodology in capturing the true dynamics of wrist movements in response to muscular actions. This understanding is pivotal in stroke rehabilitation, as it allows for a more targeted and effective approach to therapy, focusing on the specific muscles and movements that need improvement based on the individual's muscle activity patterns. It also offers valuable insights into the mechanics of movement and muscle control, enhancing the understanding of motor function and its recovery post-stroke.

Figure 8:
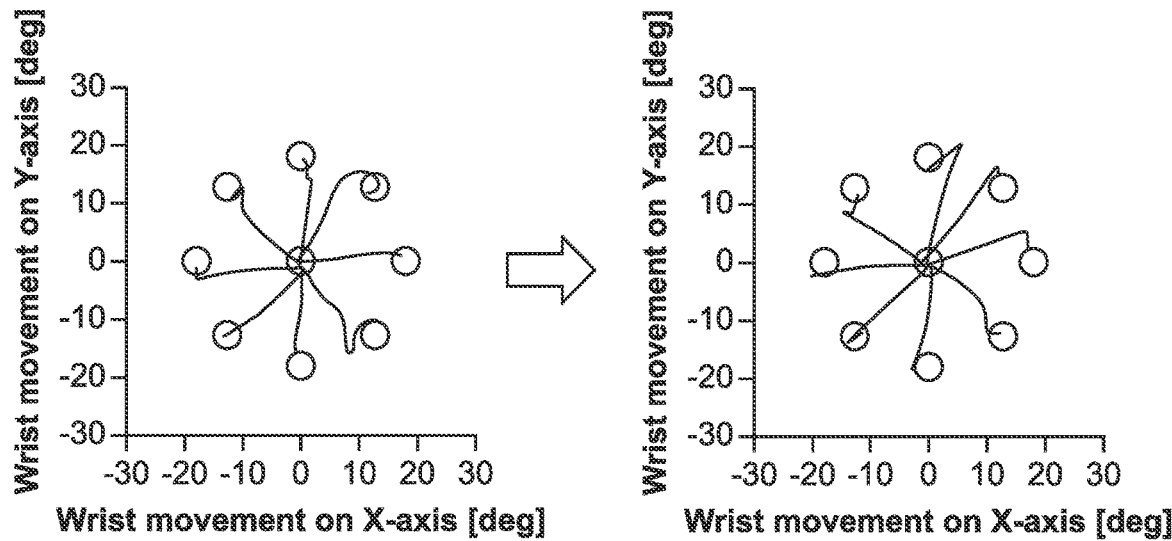
FIG. 8 is a diagram that illustrates characterization of spasticity in stroke patients using characteristic vectors, in accordance with an embodiment of the present invention.
Figure 8:
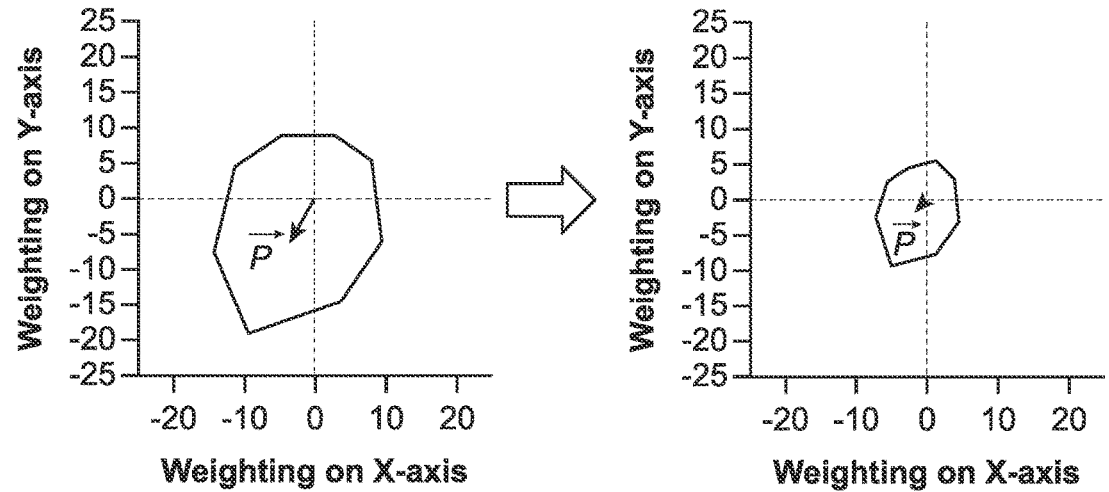

FIG. 8 is a diagram 800 that illustrates characterization of spasticity in stroke patients using characteristic vectors, in accordance with an embodiment of the present invention. A visual representation of how spasticity in stroke patients is characterized and quantified using the generated characteristic vectors. FIG. 8(A) describes changes before and after rehabilitation in the 8 directional step-tracking wrist movements. FIG. 8(B) describes characteristic vectors $\vec{P}$ changing before and after rehabilitation of stroke patients.

Understanding the characteristic vector $\vec{P}$ allows therapists to develop more targeted rehabilitation strategies. They can focus on exercises and interventions that specifically address the muscles contributing to the spasticity. For instance, if the vector indicates a dominance of flexor muscle activity pulling the wrist down and to the left, therapists might focus on exercises that strengthen the extensor muscles or employ techniques to relax and lengthen the overactive flexors. Over time, changes in the characteristic vector may be monitored to track the patient's progress. Improvements in spasticity might be indicated by a reduction in the vector's magnitude or a change in its direction, signifying a more balanced muscle activity around the wrist. The characteristic vector is a powerful tool in the context of stroke rehabilitation. It provides a quantifiable measure of spasticity, offering detailed insights into the specific muscular imbalances and tensions that affect a patient's wrist movement. By leveraging this information, clinicians can significantly improve the precision and effectiveness of rehabilitation interventions for stroke survivors.

Figure 9:
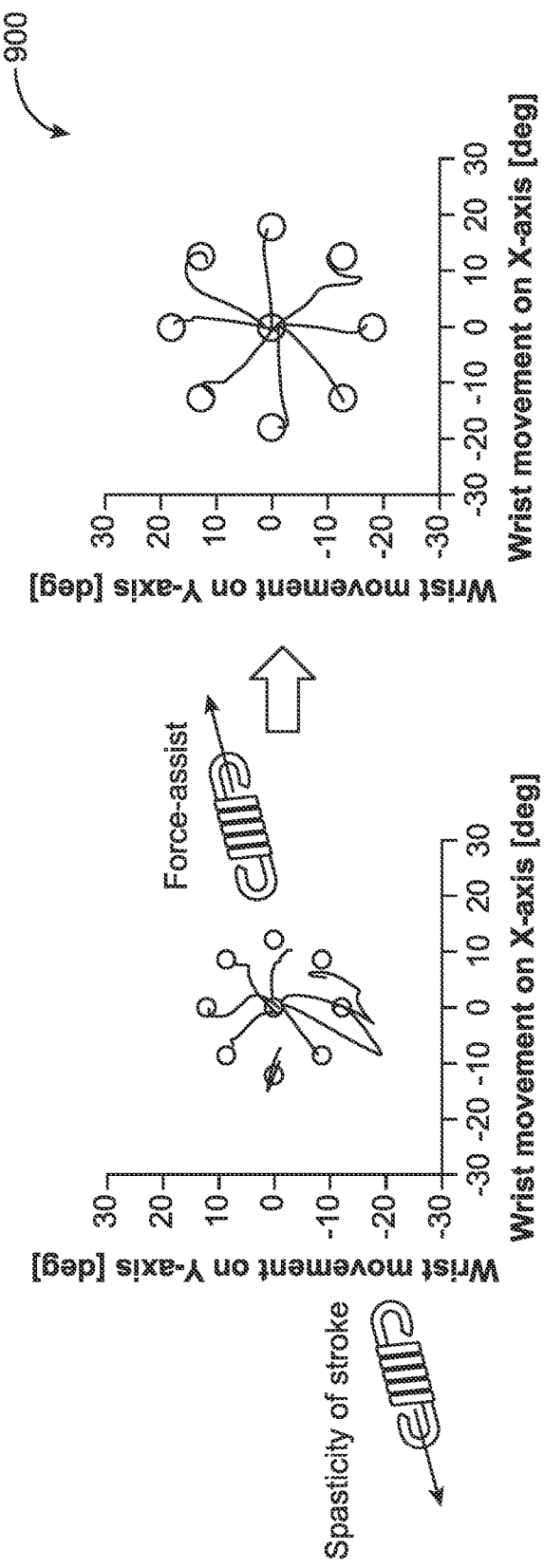
FIG. 9 is a diagram that illustrates rehabilitation support for stroke patients based on characteristic vectors, in accordance with an embodiment of the present invention.
Figure 9:
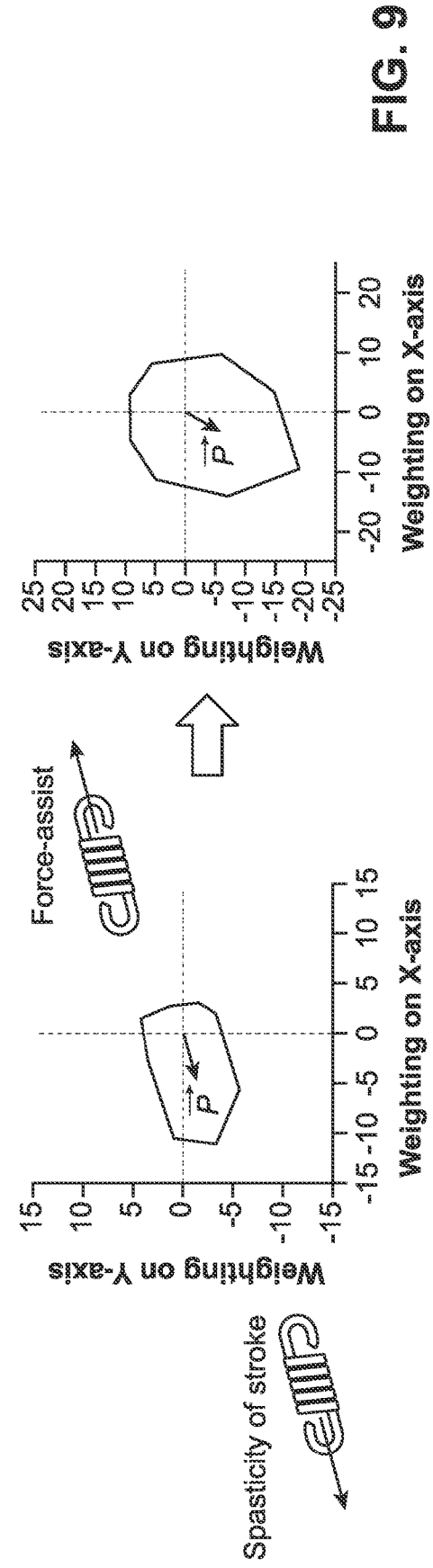

FIG. 9 is a diagram 900 that illustrates rehabilitation support for stroke patients based on characteristic vectors, in accordance with an embodiment of the present invention. Depiction of the rehabilitation support process for stroke patients, highlighting how the use of characteristic vectors aids in personalized therapy. As shown in FIG. 9, wrist movements of the stroke patient are assisted in the opposite direction of the characteristic vector $\vec{P}$ caused by spasticity of the flexor muscles, with considering the direction and magnitude of the characteristic vector $\vec{P}$ for each stroke patient. The motor devises attached on the wrist system are used for this motion support. A motorized wrist system may be used for assisting wrist movements of the stroke patient in a direction opposite to that indicated by the characteristic vector. The motorized wrist system includes motor devices capable of applying controlled forces to assist and resist the wrist movements.

Figure 10:
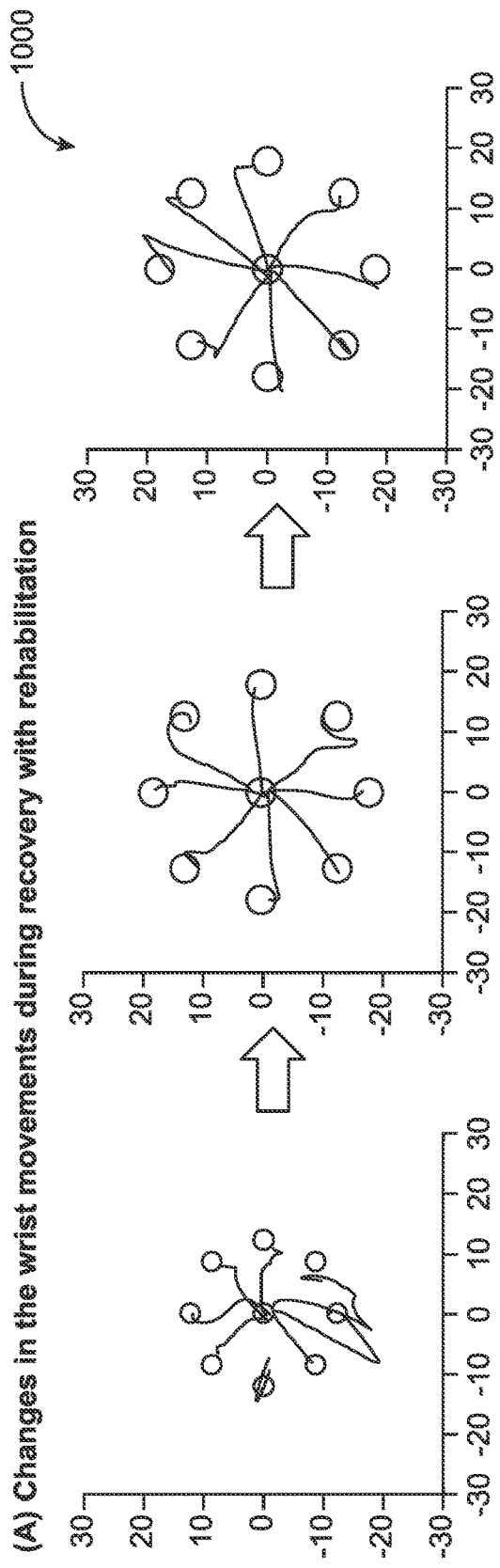
FIG. 10 is a diagram that illustrates changes in wrist movements and moment force vectors during recovery, in accordance with an embodiment of the present invention.
Figure 10:
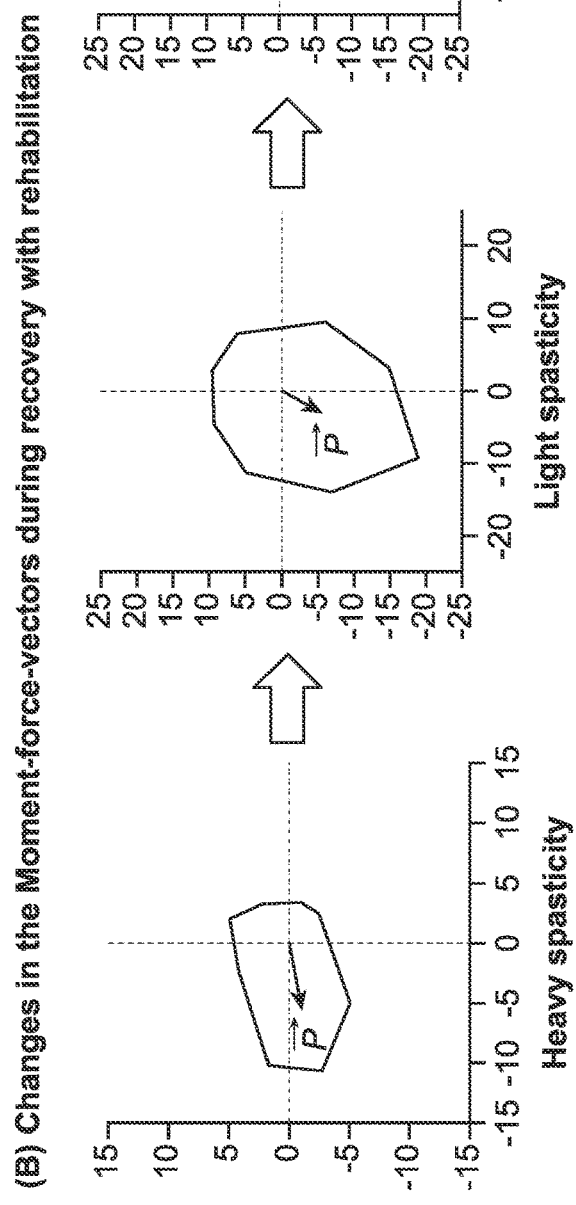
Figure 11:
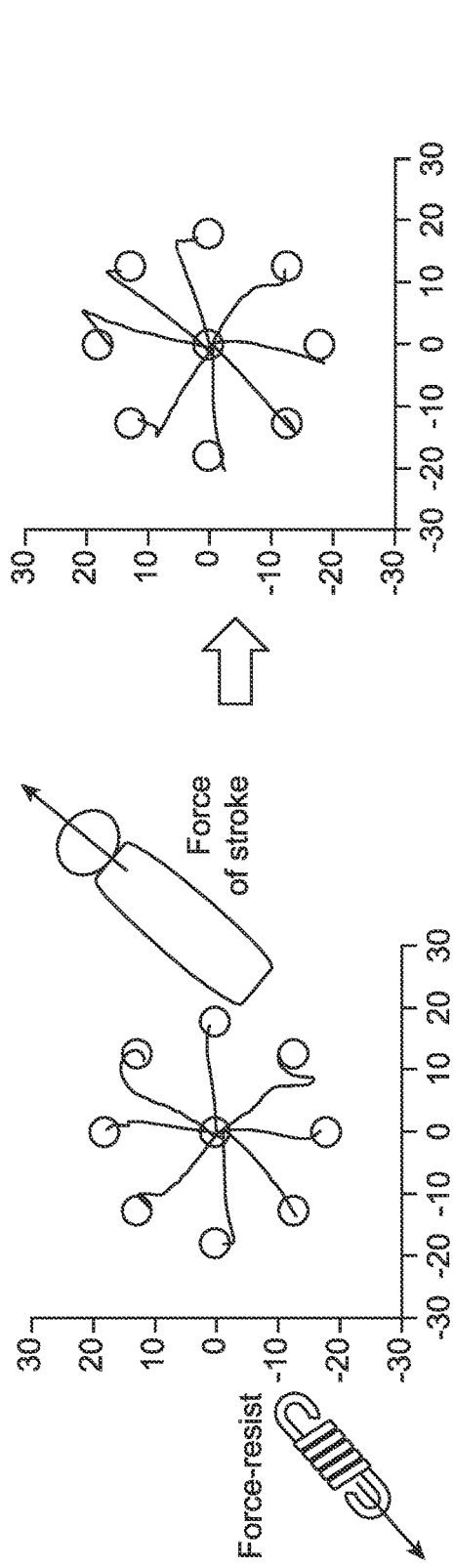
FIG. 11 is a diagram that illustrates force resistance with the wrist torque system based on the property vector, in accordance with an embodiment of the present invention.
Figure 11:
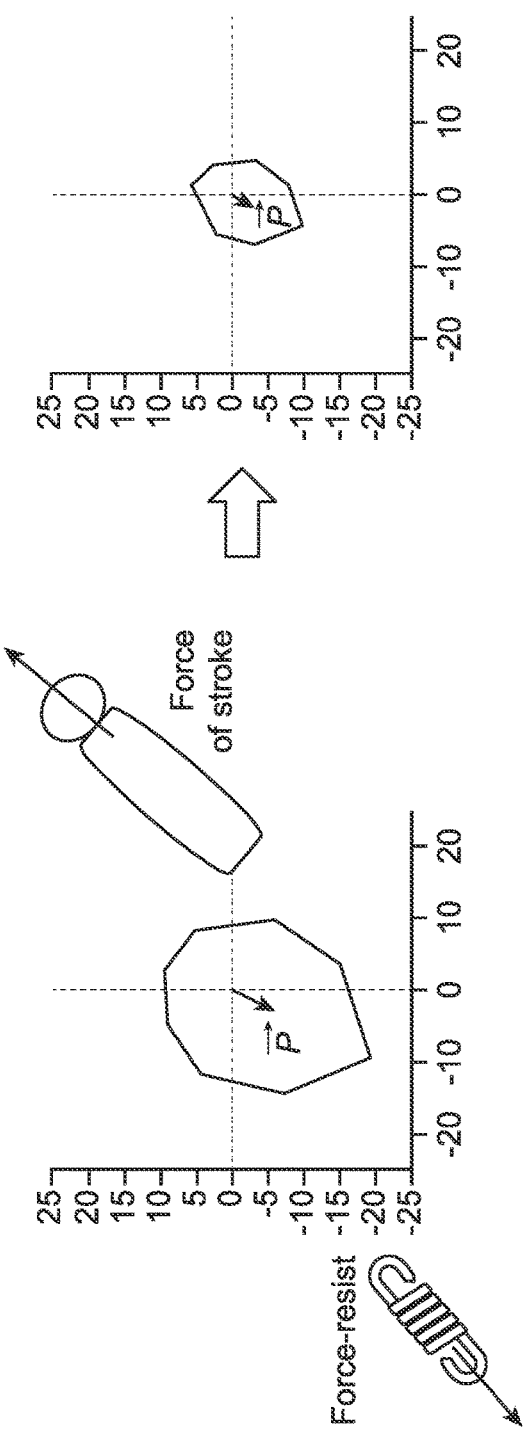

FIG. 10 is a diagram 1000 that illustrates changes in wrist movements and moment force vectors during recovery, in accordance with an embodiment of the present invention. This diagram illustrates the evolution of wrist movements and corresponding changes in moment force vectors in patients during their recovery and rehabilitation process. FIG. 11 is a diagram 1100 that illustrates force resistance with the wrist torque system based on the property vector, in accordance with an embodiment of the present invention. This is a schematic showing how the wrist torque system provides resistance based on the property vector, used to enhance rehabilitation effectiveness.

The system described is a comprehensive and advanced solution for assessing and rehabilitating spasticity in stroke patients, integrating several key components to provide a detailed analysis of muscle and wrist joint function. The set of electrodes are crucial for recording electromyography (EMG) signals. These electrodes are placed on at least eight muscles involved in wrist movements, ensuring a comprehensive capture of muscular activity. The EMG signals are essential for understanding the muscle contractions and their coordination during wrist movements, which is particularly important in stroke patients who often experience muscle control issues. The system further includes a motion tracking module. This module is responsible for accurately tracking the kinematics of the wrist joint, including parameters such as wrist angle, angular velocity, and angular acceleration. By doing so, it provides real-time data on how the wrist is moving, which is vital for understanding the mechanical aspects of wrist movements. This data complements the EMG signal data, offering a complete picture of the wrist's functional state. The system further includes a processing unit, designed to calculate wrist joint torque from the kinematic data using an equation of motion. This calculation is significant as it translates the kinematic data into quantifiable mechanical forces at the wrist joint, providing a deeper understanding of the physical effects of muscle contractions. Moreover, the processing unit is configured to normalize the recorded EMG signals based on a constant joint torque established through an isometric contraction task. This normalization process is essential for ensuring the accuracy and reliability of EMG data, as it accounts for potential variabilities such as differences in skin resistance or electrode placement. The computational module in the system plays a critical role in determining the moment arms for each muscle. This is achieved by analyzing the normalized EMG signals in conjunction with the calculated wrist joint torque, using a least squares optimization method. The moment arms are pivotal in understanding how different muscles contribute to wrist movements, providing insights into the complex dynamics of muscle function post-stroke. One of the most innovative aspects of this system is the characteristic vector calculator. This component determines a vector indicating the state of spasticity based on the moment arms. The characteristic vector is a quantifiable measure that represents the overall condition of spasticity in the patient's wrist, including its severity and directional bias. This vector is critical for tailoring the rehabilitation process to each patient's specific needs, as it highlights the muscles and movements most affected by spasticity. The system further includes the motorized wrist system, an essential component for the rehabilitation phase. This system assists the wrist movements of the stroke patient in a direction that is opposite to that indicated by the characteristic vector. By doing so, it effectively counteracts the spastic tendencies of the muscles, aiding in the restoration of balanced muscle function and wrist mobility. The motorized wrist system is a direct application of the insights gained from the EMG and kinematic analyses, allowing for targeted and effective rehabilitation exercises.

In an embodiment, the use of Ag—AgCl (silver-silver chloride) electrode pairs in the system is a strategic choice, primarily for their effectiveness in recording electromyography (EMG) signals. Ag—AgCl electrodes are known for their high conductivity and stability, which are essential qualities for capturing the subtle electrical activities generated by muscle contractions. Ag—AgCl electrodes have excellent electrical conductivity, ensuring that the minute electrical signals produced by muscle fibers during contraction are accurately captured. This feature is crucial for EMG, where the quality of the signal directly impacts the accuracy of muscle activity analysis. These electrodes also exhibit low noise characteristics, which means that they are less likely to pick up extraneous electrical signals or interference. This stability is important in clinical and rehabilitative settings, where accuracy is paramount.

In an embodiment, the inclusion of a second-order low-pass filter with a cut-off frequency of 5.0 Hz in the processing unit of the system is a crucial feature for analyzing wrist joint torque. This technical specification plays a key role in processing the electromyography (EMG) signals for assessing and rehabilitating spasticity in stroke patients. The second-order low-pass filter effectively reduces high-frequency noise, ensuring that only relevant frequencies that represent true muscle activity are analyzed. This is critical for obtaining accurate and reliable EMG data. The second-order filter provides a steeper roll-off compared to a first-order filter. This means that it more effectively attenuates frequencies above the cut-off point. In the context of EMG signal processing, this helps in isolating the true muscle activity signals from external noise. The cut-off frequency of 5.0 Hz is chosen based on the typical frequency range of interest in EMG signals for muscle activity assessment. This frequency is low enough to filter out high-frequency noise but high enough to retain the essential information contained in the EMG signals related to muscle contractions. By filtering the EMG signals, the processing unit can more accurately calculate the wrist joint torque. This torque calculation is integral to understanding the forces exerted by the muscles on the wrist joint, which is essential in assessing spasticity and planning rehabilitation exercises. The filtered EMG data, when combined with the kinematic data from the motion tracking module, provides a comprehensive view of the wrist's functionality. This integration is crucial for determining the characteristic vector and for guiding the motorized wrist system to assist in movements effectively.

In an embodiment, the use of a constant joint torque of 0.784 Nm as a baseline for the isometric contraction task provides a consistent and reliable standard against which all EMG readings are compared. During this task, the patient exerts force to maintain a wrist position that generates this specific torque, allowing the system to record EMG signals under a controlled and uniform condition. This normalization process is essential for mitigating factors such as electrode-skin impedance and variations in muscle response, leading to more accurate assessments of muscle activity. By standardizing the EMG signals in this manner, the system can effectively calibrate its readings, ensuring that subsequent analyses, such as the calculation of the characteristic vector and the adjustment of the motorized wrist system, are based on precise and reliable data. This approach enhances the system's overall ability to assess spasticity accurately and to tailor rehabilitation exercises to the specific needs of stroke patients.

In an embodiment, the inclusion of terms representing moment of inertia, viscosity, and elasticity coefficients in the equation of motion, and the configuration of the processing unit to use pre-defined values for these coefficients, highlight the system's comprehensive approach to modeling wrist joint mechanics. This approach is pivotal in accurately calculating the wrist joint torque, which is a critical component of the system's function in assessing and rehabilitating spasticity in stroke patients. By configuring the processing unit to utilize pre-defined values for these coefficients, the system standardizes a complex aspect of biomechanical assessment. This standardization is essential for making the system's assessments and rehabilitative recommendations consistent and reliable. It ensures that the calculated wrist joint torque, which forms the basis for assessing spasticity and guiding the motorized wrist system, accurately reflects the interplay of muscular forces and the mechanical properties of the wrist joint. In summary, this aspect of the system allows for a nuanced and precise analysis of wrist mechanics, crucial for effective spasticity management in stroke rehabilitation.

The computational module's use of the least squares optimization method for determining the moment arms of each muscle involved in wrist movements is a key feature in the system designed for assessing and rehabilitating spasticity in stroke patients. Moment arms are crucial biomechanical parameters that represent the distance between the muscle's line of action and the joint center, influencing how muscle forces translate into joint movement and torque. Accurately determining these moment arms is essential for understanding the mechanics of wrist movements, particularly in stroke patients who may experience altered muscle function and coordination. The least squares optimization method is a mathematical technique used to find the best-fit solution to a set of equations, minimizing the sum of the squares of the differences between observed and calculated values. In the context of this system, the method is employed to correlate the recorded EMG signals (indicative of muscle activity) with the wrist joint torque, calculated from the kinematic data. By applying this optimization technique, the computational module can precisely determine how each muscle contributes to wrist movements, accounting for individual variations in muscle strength and control. This detailed analysis is crucial for the system to accurately assess the state of spasticity and to tailor rehabilitation exercises effectively. The use of least squares optimization ensures that the system's assessments and recommendations are based on a robust and accurate biomechanical model of the patient's wrist, enhancing the efficacy of the rehabilitation process.

In an embodiment, the characteristic vector calculator within the system plays a pivotal role in assessing spasticity in stroke patients by computing a vector that encapsulates the combined effects of muscle actions on wrist movement. This is achieved by using the linear sum of the moment arms of each muscle involved in wrist movements, calculated for both X and Y axes. Moment arms represent the effectiveness of muscle forces in causing rotation at the wrist joint; thus, their summation across different muscles provides a comprehensive view of the overall muscle influence on wrist motion. The characteristic vector, derived from these summed moment arms, effectively represents the net biomechanical influence exerted by all the muscles on the wrist joint in both the horizontal and vertical planes. The utility of the characteristic vector extends beyond a mere biomechanical representation; it serves as a crucial tool in assessing the severity and direction of spasticity in a stroke patient's wrist. Spasticity, characterized by increased muscle tone and overactive reflexes, can significantly impair wrist movement and function. By analyzing the characteristic vector, clinicians can gain insights into which muscles are contributing most to the spasticity, as well as the direction in which the wrist is predominantly being pulled or restricted. This detailed understanding of the spasticity's nature allows for more targeted and effective rehabilitation strategies. It enables therapists to design exercises and interventions that specifically address the identified muscular imbalances and movement restrictions, thereby improving the efficacy of the rehabilitation process and enhancing recovery outcomes for stroke survivors.

In an embodiment, the inclusion of a visual feedback interface in the system adds a significant dimension to the rehabilitation process for stroke patients, enhancing their engagement and understanding of the therapy. This interface is configured to display real-time wrist movements, translating the physical movements of the patient's wrist into corresponding cursor movements on a screen. By providing a visual representation of wrist actions, the interface creates an intuitive and interactive platform for patients to visualize their movements in real-time. This feature is especially beneficial in facilitating motor learning and reinforcing correct movement patterns, which are critical aspects of rehabilitation for stroke survivors. The representation of wrist movements as cursor movements on a screen makes the rehabilitation exercises more engaging and understandable for patients. This visual feedback allows patients to immediately see the results of their efforts, encouraging active participation in the therapy process. It also aids therapists in monitoring and guiding the patient's progress, as the screen display offers a clear and immediate depiction of both correct movements and areas needing improvement. Additionally, this visual feedback mechanism can be particularly motivating for patients, as it provides a tangible way to track progress and improvement over time. In essence, the visual feedback interface serves as a bridge between the physical and cognitive aspects of rehabilitation, enhancing the overall efficacy and experience of the therapy.

In an embodiment, the motorized wrist system is a critical component of the rehabilitation system, designed to provide active assistance to the wrist movements of stroke patients. This system incorporates motor devices capable of applying controlled forces, which are essential for assisting the wrist in movements that the patient might struggle with due to spasticity or muscle weakness. The motor devices are engineered to deliver precise and varying levels of force, enabling them to assist in flexion, extension, and other necessary movements of the wrist. This active assistance not only aids in performing the movements but also helps in strengthening the muscles and improving the range of motion over time. The controlled nature of the forces ensures that the assistance is provided in a manner that is both safe and beneficial for the patient, aligning with their specific therapeutic needs. A key feature of these motor devices is their programmability, allowing for the customization of the extent and direction of the applied forces. This programmability is vital as it enables the system to adapt to the patient's rehabilitation progress. As the patient's condition improves, the level of assistance can be adjusted accordingly, gradually reducing the support as the patient regains strength and control. This adaptability ensures that the therapy remains challenging yet achievable, promoting continuous improvement in wrist function. The ability to program and adjust the motor devices ensures that the rehabilitation process is dynamic and responsive to the changing needs of the patient, making the therapy more effective and aligned with the patient's recovery journey.

The present invention, which focuses on assessing and rehabilitating spasticity in stroke patients through the use of characteristic vectors derived from EMG signals and wrist movement kinematics, offers several notable advantages and applications: (1) Traditional methods of assessing spasticity are often subjective and may vary between clinicians. This invention provides an objective and quantifiable means of assessing spasticity by analyzing the causal relationship between EMG signals and wrist movements. The use of characteristic vectors offers a precise, numerical way to measure the severity and nature of spasticity. (2) By calculating the characteristic vector for each patient, the system can tailor rehabilitation exercises to address specific muscle imbalances and movement restrictions. This personalization ensures that therapy is more effective and directly targets the patient's unique challenges, enhancing the recovery process. (3) The invention allows for real-time monitoring and adjustment of the rehabilitation process. Motor devices attached to the wrist system can adapt the movement assistance based on the patient's progress, ensuring that the therapy remains optimally challenging and beneficial throughout the rehabilitation period. (4) The invention contributes significantly to the understanding of muscle dynamics in stroke patients. By correlating EMG data with kinematic measurements, it provides insights into how different muscles contribute to movement disorders like spasticity, which can inform future research and treatment approaches.

The primary application of this invention is in the field of stroke rehabilitation. It can be used in clinical settings to assess and treat patients who have experienced a stroke, particularly those suffering from spasticity and other motor function impairments. The system's ability to provide targeted therapy based on individual muscle activity makes it a valuable tool for improving motor control and reducing the impact of spasticity. This invention has potential applications in research, particularly in the fields of neurophysiology and biomechanics. Researchers can use it to study the mechanisms underlying muscle control and movement disorders, contributing to a deeper understanding of conditions like stroke and other neurological disorders. The principles and technology underlying this invention could inform the development of more advanced therapeutic devices and systems. For instance, the integration of EMG analysis with motor-assisted movement can be applied to the development of exoskeletons or other assistive technologies for broader range of movement disorders. The invention can also serve as a training and assessment tool for physical therapists, occupational therapists, and other healthcare professionals. By providing objective data and clear visualizations of muscle activity and movement patterns, it can enhance the training of professionals in diagnosing and treating motor impairments. With advancements in technology, a version of this system could potentially be adapted for home use, allowing patients to continue their rehabilitation exercises outside of clinical settings. This can be particularly beneficial for long-term rehabilitation, offering patients more flexibility and autonomy in their recovery process.

Although the present invention has been described with respect to various schematic representations (FIGS. 1-11), it should be understood that the proposed design may be realized and implemented with varying shapes and sizes, and thus the present invention here should not be considered limited to the exemplary embodiments and processes described herein. The various dimensions may be modified to fit in specific application areas. Although particular embodiments of the invention have been described in detail for purposes of illustration, various modifications and enhancements may be made without departing from the spirit and scope of the invention.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. A person having ordinary skills in the art may implement the described functionality in varying ways for each application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A system for assessing and rehabilitating spasticity in stroke patients, comprising:
   a set of electrodes for recording eight electromyography (EMG) signals from at least four muscles involved in wrist movements;
   a motion tracking module for tracking the kinematics of wrist joint motion including wrist angle, angular velocity, and angular acceleration;
   a processing unit configured to calculate wrist joint torque based on the kinematics using an equation of motion and to normalize the recorded EMG signals based on a constant joint torque using an isometric contraction task;
   a computational module for determining moment arms for each muscle based on the normalized EMG signals and the calculated wrist joint torque using a least squares optimization method;
   a characteristic vector calculator for determining a vector indicating the state of spasticity based on the moment arms, wherein the characteristic vector calculator computes the vector using the linear sum of the moment arms of each muscle in both X and Y axes of the wrist movement; and
   a motorized wrist system for assisting wrist movements of the stroke patient in a direction opposite to that indicated by the characteristic vector.

2. The system of claim 1, wherein the electrodes are electrode pairs.

3. The system of claim 1, wherein the processing unit is further configured to calculate wrist joint torque using a bandwidth-pass filter with a 0.01~2.5 Hz.

4. The system of claim 1, wherein the isometric contraction task for normalization is based on a constant joint torque, the around maximum exertable torque by a patient.

5. The system of claim 1, wherein the equation of motion includes terms representing moment of inertia, viscosity, and elasticity coefficients of the wrist, and the processing unit is configured to use pre-defined values for these coefficients.

6. The system of claim 5, wherein the viscosity coefficient has a unit of measurement of Nms/rad and the elasticity coefficient has a unit of measurement of Nm/rad, and wherein the elasticity coefficient and the viscosity coefficient are used to determine wrist joint torque.

7. The system of claim 1, wherein the computational module uses the least squares optimization method for determining the moment arms of each muscle involved in the wrist movements.

8. The system of claim 1, wherein the characteristic vector is used to assess the severity and direction of spasticity in the wrist of the stroke patient.

9. The system of claim 1, further comprising a visual feedback interface configured to display real-time wrist movements.

10. The system of claim 9, wherein the visual feedback interface represents wrist movements as cursor movements on a screen, corresponding to actual wrist movements.

11. The system of claim 1, wherein the motorized wrist system includes motor devices capable of applying controlled forces to assist and resist the wrist movements.

12. The system of claim 11, wherein the motor devices are programmable to adjust the extent and direction of the applied forces based on the patient's rehabilitation progress.

13. The system of claim 1, configured for use in both clinical and home-based rehabilitation settings.

14. The system of claim 1, further configured to serve as a training tool for healthcare professionals in diagnosing and treating motor impairments related to stroke.

15. A system for assessing and rehabilitating spasticity in stroke patients, comprising:
   a set of electrodes for recording eight electromyography (EMG) signals from at least four muscles involved in wrist movements;
   a motion tracking module for tracking the kinematics of wrist joint motion including wrist angle, angular velocity, and angular acceleration;
   a processing unit configured to calculate wrist joint torque based on the kinematics using an equation of motion and to normalize the recorded EMG signals based on a constant joint torque using an isometric contraction task;
   a computational module for determining moment arms for each muscle based on the normalized EMG signals and the calculated wrist joint torque using a least squares optimization method;
   a characteristic vector calculator for determining a vector indicating the state of spasticity based on the moment arms, wherein the characteristic vector calculator computes the vector using the linear sum of the moment arms of each muscle in both X and Y axes of the wrist movement;
   a motorized wrist system for assisting wrist movements of the stroke patient in a direction opposite to that indicated by the characteristic vector; and
   wherein the equation of motion includes terms representing moment of inertia, viscosity, and elasticity coefficients of the wrist, and the processing unit is configured to use pre-defined values for these coefficients.

16. The system of claim 15, wherein the viscosity coefficient has a unit of measurement of Nms/rad and the elasticity coefficient has a unit of measurement of Nm/rad, and wherein the elasticity coefficient and the viscosity coefficient are used to determine wrist joint torque.

17. The system of claim 15, wherein the viscosity coefficient is set to 0.03 Nms/rad and the elasticity coefficient is set to 0.2 Nm/rad.

18. The system of claim 15, wherein the viscosity coefficient is adjusted to be within the range of 0.1 to 1.5 for the elasticity coefficient based on the task and individual performance.

* * * * *